(12) United States Patent
Sicotte et al.

(10) Patent No.: US 10,292,833 B2
(45) Date of Patent: May 21, 2019

(54) STRUCTURALLY SUPPORTING INSERT FOR SPINAL FUSION CAGE

(71) Applicant: Howmedica Osteonics Corp., Mahwah, NJ (US)

(72) Inventors: Marcel Sicotte, San Francisco, CA (US); Damien J. Shulock, San Francisco, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 857 days.

(21) Appl. No.: 14/554,684

(22) Filed: Nov. 26, 2014

(65) Prior Publication Data

US 2015/0148906 A1    May 28, 2015

Related U.S. Application Data

(60) Provisional application No. 61/909,667, filed on Nov. 27, 2013.

(51) Int. Cl.
*A61F 2/44* (2006.01)
*A61F 2/46* (2006.01)
(Continued)

(52) U.S. Cl.
CPC .............. *A61F 2/447* (2013.01); *A61F 2/442* (2013.01); *A61F 2/4611* (2013.01); *A61F 2/4601* (2013.01); *A61F 2002/30331* (2013.01); *A61F 2002/30556* (2013.01); *A61F 2002/30601* (2013.01); *A61F 2002/30733* (2013.01); *A61F 2002/30774* (2013.01);
(Continued)

(58) Field of Classification Search
CPC ....... A61F 2/44; A61F 2/46; A61F 2002/4629
USPC ............................... 623/17.11–17.16; 606/99
See application file for complete search history.

(56) References Cited

U.S. PATENT DOCUMENTS 3,875,595 A    4/1975  Froning
4,932,975 A    6/1990  Main et al.
(Continued)

FOREIGN PATENT DOCUMENTS

JP    2010522609 A    7/2010
JP    2012505068 A    3/2012
(Continued)

OTHER PUBLICATIONS

International Search Report and Written Opinion for Application No. PCT/US2014/067683 dated Feb. 12, 2015.

*Primary Examiner* — David W Bates
(74) *Attorney, Agent, or Firm* — Lerner, David, Littenberg, Krumholz & Mentlik, LLP (57) ABSTRACT

An expandable implant includes a structural insert to provide a robust connection between an insertion instrument and the expandable implant. The structural insert can be made from a different material than the remainder of the implant to withstand compressive, tensile, shear, and torsional loads which may be present while inserting the implant into a patient. The structural insert may be formed as part of a bottom member of the implant or may be a separate element inserted into the implant body. The structural insert may provide a threaded connection to an insertion instrument. The expandable implant may include a bone graft port in fluid communication with a bone graft opening extending through the implant body.

19 Claims, 6 Drawing Sheets

(51) Int. Cl.
*A61F 2/48* (2006.01)
*A61F 2/30* (2006.01)

(52) U.S. Cl.
CPC ............ *A61F 2002/30836* (2013.01); *A61F 2002/4475* (2013.01); *A61F 2002/4629* (2013.01); *A61F 2002/4693* (2013.01); *A61F 2002/485* (2013.01); *A61F 2310/00017* (2013.01); *A61F 2310/00023* (2013.01); *A61F 2310/00029* (2013.01)

(56) References Cited

U.S. PATENT DOCUMENTS

| | | | |
|---|---|---|---|
| 5,236,460 A | 8/1993 | Barber | |
| 5,653,763 A | 8/1997 | Errico et al. | |
| 5,665,122 A | 9/1997 | Kambin | |
| 5,980,522 A | 11/1999 | Koros et al. | |
| 6,039,761 A | 3/2000 | Li et al. | |
| 6,127,597 A | 10/2000 | Beyar et al. | |
| 6,193,756 B1 | 2/2001 | Studer et al. | |
| 6,375,682 B1 | 4/2002 | Fleischmann et al. | |
| 6,395,032 B1 | 5/2002 | Gauchet | |
| 6,454,806 B1 | 9/2002 | Cohen et al. | |
| 6,582,467 B1 | 6/2003 | Teitelbaum et al. | |
| 6,585,699 B2 | 7/2003 | Ljunggreen et al. | |
| 6,692,495 B1 | 2/2004 | Zacouto | |
| 6,719,796 B2 | 4/2004 | Cohen et al. | |
| 6,723,126 B1 | 4/2004 | Berry | |
| 6,764,491 B2 | 7/2004 | Frey et al. | |
| 6,830,570 B1 | 12/2004 | Frey et al. | |
| 6,835,207 B2 | 12/2004 | Zacouto et al. | |
| 6,866,682 B1 | 3/2005 | An et al. | |
| 6,953,477 B2 | 10/2005 | Berry | |
| 6,960,232 B2 | 11/2005 | Lyons et al. | |
| 6,981,989 B1 | 1/2006 | Fleischmann et al. | |
| 7,001,431 B2 | 2/2006 | Bao et al. | |
| 7,018,416 B2 | 3/2006 | Hanson et al. | |
| 7,060,073 B2 | 6/2006 | Frey et al. | |
| 7,066,958 B2 | 6/2006 | Ferree | |
| 7,166,110 B2 | 1/2007 | Yundt | |
| 7,204,853 B2 | 4/2007 | Gordon et al. | |
| 7,217,293 B2 | 5/2007 | Branch, Jr. | |
| 7,282,063 B2 | 10/2007 | Cohen et al. | |
| 7,291,150 B2 | 11/2007 | Graf | |
| 7,351,261 B2 | 4/2008 | Casey | |
| 7,407,513 B2 | 8/2008 | Alleyne et al. | |
| 7,419,505 B2 | 9/2008 | Fleischmann et al. | |
| 7,452,359 B1 | 11/2008 | Michelson | |
| 7,470,273 B2 | 12/2008 | Dougherty-Shah | |
| 7,481,812 B2 | 1/2009 | Frey et al. | |
| 7,485,145 B2 | 2/2009 | Purcell | |
| 7,507,241 B2 | 3/2009 | Levy et al. | |
| 7,520,900 B2 | 4/2009 | Trieu | |
| 7,563,284 B2 | 7/2009 | Coppes et al. | |
| 7,563,286 B2 | 7/2009 | Gerber et al. | |
| 7,621,956 B2 | 11/2009 | Paul et al. | |
| 7,628,815 B2 | 12/2009 | Baumgartner et al. | |
| 7,670,359 B2 | 3/2010 | Yundt | |
| 7,708,779 B2 | 5/2010 | Edie et al. | |
| 7,722,674 B1 | 5/2010 | Grotz | |
| 7,731,752 B2 | 6/2010 | Edie et al. | |
| 7,731,753 B2 | 6/2010 | Reo et al. | |
| 7,771,480 B2 | 8/2010 | Navarro et al. | |
| 7,794,501 B2 | 9/2010 | Edie et al. | |
| 7,806,935 B2 | 10/2010 | Navarro et al. | |
| 7,819,921 B2 | 10/2010 | Gratz | |
| 7,824,444 B2 | 11/2010 | Biscup et al. | |
| 7,824,445 B2 | 11/2010 | Biro et al. | |
| 7,862,618 B2 | 1/2011 | White et al. | |
| 7,935,124 B2 | 5/2011 | Frey et al. | |
| 7,967,863 B2 | 6/2011 | Frey et al. | |
| 7,967,867 B2 | 6/2011 | Barreiro et al. | |
| 7,985,231 B2 | 7/2011 | Sankaran | |
| 7,985,256 B2 | 7/2011 | Gratz et al. | |
| 8,021,395 B2 | 9/2011 | Ben-Mokhtar et al. | |
| 8,025,680 B2 | 9/2011 | Hayes et al. | |
| 8,057,549 B2 | 11/2011 | Butterman et al. | |
| 8,062,368 B2 | 11/2011 | Heinz et al. | |
| 8,062,373 B2 | 11/2011 | Fabian, Jr. | |
| 8,070,813 B2 | 12/2011 | Grotz et al. | |
| 8,105,382 B2 | 1/2012 | Olmos et al. | |
| 8,153,785 B2 | 4/2012 | Khire et al. | |
| 8,187,331 B2 | 5/2012 | Strohkirch, Jr. et al. | |
| 8,192,495 B2 | 6/2012 | Simpson et al. | |
| 8,267,939 B2 | 9/2012 | Cipoletti et al. | |
| 8,273,124 B2 | 9/2012 | Renganath et al. | |
| 8,353,961 B2 | 1/2013 | McClintock et al. | |
| 8,366,777 B2 | 2/2013 | Matthis et al. | |
| 8,394,143 B2 | 3/2013 | Grotz et al. | |
| 8,435,296 B2 | 5/2013 | Kadaba et al. | |
| 8,535,357 B2 * | 9/2013 | Stone | A61B 17/866 606/300 |
| 8,696,751 B2 | 4/2014 | Ashley et al. | |
| 9,155,628 B2 * | 10/2015 | Glerum | A61F 2/4455 |
| 9,265,621 B2 * | 2/2016 | Voellmicke | A61F 2/447 |
| 9,554,918 B2 * | 1/2017 | Weiman | A61F 2/442 |
| 9,974,664 B2 * | 5/2018 | Emerick | A61F 2/447 |
| 9,980,824 B2 * | 5/2018 | Zappacosta | A61F 2/4455 |
| 10,039,650 B2 * | 8/2018 | Lamborne | A61F 2/4425 |
| 10,098,758 B2 * | 10/2018 | Matthews | A61F 2/4425 |
| 10,159,584 B2 * | 12/2018 | Carnes | A61F 2/4611 |
| 2002/0128716 A1 | 9/2002 | Cohen et al. | |
| 2002/0183859 A1 * | 12/2002 | Houser | A61F 2/7812 623/36 |
| 2004/0030346 A1 | 2/2004 | Frey et al. | |
| 2004/0186576 A1 | 9/2004 | Biscup et al. | |
| 2005/0043800 A1 | 2/2005 | Paul et al. | |
| 2005/0197702 A1 | 9/2005 | Coppes et al. | |
| 2005/0216084 A1 | 9/2005 | Fleischmann et al. | |
| 2005/0228501 A1 * | 10/2005 | Miller | A61F 2/44 623/17.14 |
| 2005/0251260 A1 | 11/2005 | Gerber et al. | |
| 2006/0074488 A1 * | 4/2006 | Abdou | A61F 2/44 623/17.11 |
| 2006/0085071 A1 * | 4/2006 | Lechmann | A61B 17/86 623/17.11 |
| 2006/0089719 A1 | 4/2006 | Trieu | |
| 2006/0116767 A1 | 6/2006 | Magerl et al. | |
| 2006/0142860 A1 | 6/2006 | Navarro et al. | |
| 2006/0149377 A1 | 7/2006 | Navarro et al. | |
| 2006/0264968 A1 | 11/2006 | Frey et al. | |
| 2007/0050033 A1 | 3/2007 | Reo et al. | |
| 2007/0073395 A1 | 3/2007 | Baumgartner et al. | |
| 2007/0093903 A1 | 4/2007 | Cheng | |
| 2007/0179611 A1 | 8/2007 | DiPoto et al. | |
| 2007/0233254 A1 | 10/2007 | Grotz et al. | |
| 2007/0255413 A1 | 11/2007 | Edie et al. | |
| 2007/0255415 A1 | 11/2007 | Edie et al. | |
| 2007/0270961 A1 | 11/2007 | Ferguson | |
| 2007/0270964 A1 | 11/2007 | Strohkirch et al. | |
| 2007/0288092 A1 | 12/2007 | Bambakidis | |
| 2008/0021555 A1 | 1/2008 | White et al. | |
| 2008/0021556 A1 | 1/2008 | Edie | |
| 2008/0058930 A1 | 3/2008 | Edie et al. | |
| 2008/0058931 A1 | 3/2008 | White et al. | |
| 2008/0086276 A1 | 4/2008 | Naka et al. | |
| 2008/0091211 A1 * | 4/2008 | Gately | A61B 17/1671 606/99 |
| 2008/0097441 A1 | 4/2008 | Hayes et al. | |
| 2008/0103601 A1 | 5/2008 | Biro et al. | |
| 2008/0140207 A1 | 6/2008 | Olmos et al. | |
| 2008/0147193 A1 | 6/2008 | Matthis et al. | |
| 2008/0154377 A1 * | 6/2008 | Voellmicke | A61F 2/4455 623/17.16 |
| 2008/0161927 A1 * | 7/2008 | Savage | A61F 2/4455 623/17.16 |
| 2008/0161933 A1 | 7/2008 | Grotz et al. | |
| 2008/0215153 A1 | 9/2008 | Butterman et al. | |
| 2008/0221695 A1 * | 9/2008 | Jacofsky | A61F 2/447 623/17.16 |
| 2008/0288073 A1 * | 11/2008 | Renganath | A61F 2/441 623/17.12 |
| 2008/0300598 A1 | 12/2008 | Barreiro et al. | |

(56) References Cited

U.S. PATENT DOCUMENTS

| | | |
|---|---|---|
| 2009/0005819 A1 | 1/2009 | Ben-Mokhtar et al. |
| 2009/0005874 A1 | 1/2009 | Fleischmann et al. |
| 2009/0018661 A1 | 1/2009 | Kim et al. |
| 2009/0048676 A1 | 2/2009 | Fabian, Jr. |
| 2009/0105836 A1 | 4/2009 | Frey et al. |
| 2009/0171389 A1 | 7/2009 | Sankaran |
| 2009/0192611 A1 | 7/2009 | Lindner |
| 2009/0192615 A1* | 7/2009 | Tyber ............... A61F 2/442 623/17.16 |
| 2009/0204215 A1* | 8/2009 | McClintock ......... A61F 2/44 623/17.11 |
| 2009/0216331 A1 | 8/2009 | Gratz et al. |
| 2010/0042221 A1* | 2/2010 | Boyd ............... A61F 2/28 623/17.16 |
| 2010/0094422 A1 | 4/2010 | Hansell et al. |
| 2010/0145455 A1 | 6/2010 | Simpson et al. |
| 2011/0130835 A1* | 6/2011 | Ashley ............. A61F 2/442 623/17.11 |
| 2012/0010472 A1 | 1/2012 | Spann |
| 2012/0271423 A1* | 10/2012 | Wallenstein ....... A61B 17/8685 623/17.16 |
| 2013/0023937 A1* | 1/2013 | Biedermann ....... A61F 2/4465 606/279 |
| 2013/0110247 A1* | 5/2013 | Doran ............. A61F 2/3094 623/17.16 |
| 2015/0018957 A1* | 1/2015 | Nichols ............ A61F 2/4611 623/17.16 |
| 2016/0199193 A1* | 7/2016 | Willis ................ A61F 2/44 623/17.16 |
| 2017/0135706 A1* | 5/2017 | Frey ............... A61B 17/1703 |

FOREIGN PATENT DOCUMENTS

| | | |
|---|---|---|
| JP | 2013595 A | 1/2013 |
| JP | 2013526396 A | 6/2013 |
| WO | 2006044786 A2 | 4/2006 |
| WO | 2007022021 A1 | 2/2007 |
| WO | 2008039811 A2 | 4/2008 |
| WO | 2008086276 A2 | 7/2008 |
| WO | 2008112607 A2 | 9/2008 |
| WO | 2008121251 A2 | 10/2008 |
| WO | 2008148210 A1 | 12/2008 |
| WO | 2009033100 A1 | 3/2009 |
| WO | 2009105182 A1 | 8/2009 |

* cited by examiner

STRUCTURALLY SUPPORTING INSERT FOR SPINAL FUSION CAGE

CROSS-REFERENCE TO RELATED APPLICATIONS

This application claims benefit of U.S. Provisional Patent Application No. 61/909,667, filed Nov. 27, 2013, the disclosure of which is incorporated by reference herein.

BACKGROUND OF THE INVENTION

The present invention generally relates to medical devices for stabilizing the vertebral motion segment. More particularly, the present invention relates to a composite spinal intervertebral body cage for distraction and fusion.

Certain known spine cages or implants are characterized by a body comprising a hydroxyapetite coated surface provided on the exterior surface for contact with adjacent vertebral segments or endplates. A cage of this type may be inserted posteriorly through the neuroforamen of the distracted spine after a surgeon removes disc, bone, and ligament material to create a pathway.

Such existing devices for interbody stabilization have important and significant limitations. Current devices for interbody stabilization include static spacers composed of titanium, PEEK, and high performance thermoplastic polymer produced by VICTREX, (Victrex USA Inc, 3A Caledon Court; Greenville, S.C. 29615), carbon fiber, or resorbable polymers.

One problem with conventional devices for interbody stabilization made of PEEK, other high performance thermoplastics or resorbable polymers is the relative weakness and/or brittleness of these materials compared to the forces required to insert the device between bones of the spinal column. A review of the Food and Drug Administration's Medical Device Reporting (MDR) database for intervertebral body cages show that the greatest reported failure rate, at 36% of all reports, is for breakage of the cage during insertion. Therefore there is a need for intervertebral body cages made from materials that can withstand the insertion forces without breaking.

The failure point for most cages experiencing breakage during insertion is the point of attachment between the intervertebral body cage and the inserter attached to the cage which is used to place the cage between the vertebrae. There are many means know to those skilled in the art for attaching a spinal fusion cage to an insertion instrument, including, but not limited to a threaded hole and threaded screw, an impression or indentation and hooks or projections, and a supporting surface and a clamping mechanism. In all cases, the attaching means must not only secure the spinal fusion cage to the inserter and then release the cage once it is properly located in the intervertebral space, but the attaching means must also provide a secure attachment during the insertion step when significant forces may be required to advance the cage between vertebral bodies that have come in contact or near contact around a "collapsed" disc space.

Impact loads of greater than 50 pounds force have been measured during the insertion of intervertebral spinal cages between vertebrae. Even more challenging can be the rotational moments placed on the implant as it is forced into a rigidly defined space as more than 90 inch-pounds of torque have been recorded during insertion. Therefore there is a need for intervertebral body cages with robust insertion attachment which can withstand the insertion forces without separation.

BRIEF SUMMARY OF THE INVENTION

An expandable implant according to one aspect of the disclosure preferably comprises a body having an attachment port and a bone graft port, a top member moveable with respect to the body, and a structural insert positioned at least partially within the body and configured to couple to an insertion instrument, wherein the structural insert is made from a different material than the body.

An expandable implant according to another aspect of the disclosure comprises a body having an attachment port and a bone graft port, a top member, a bottom member, and a structural insert coupled to the bottom member and configured to couple to an insertion instrument, wherein the structural insert is made from a different material than the body.

The body may be constructed of a polymer and the structural insert constructed of metal. The body could also be composed of PEEK and the insert could be one of titanium alloy, stainless steel alloy, and cobalt chromium alloy.

An expandable implant can be configured to expand hydraulically. The body may have a bone graft opening extending through the top member and body, wherein the bone graft port is in fluid communication with the bone graft opening. An expandable implant can also have a torque resistant port formed in the body configured to couple to a tab on an insertion instrument to prevent the body from rotating relative to the insertion instrument. In at least one embodiment, the structural insert can provide a threaded connection with an insertion instrument. The attachment port may have a smooth surface and be concentric with a threaded opening of the structural insert. The body can have an opening into which the structural insert is placed.

A method of inserting an expandable implant according to one aspect of the disclosure comprises providing an expandable implant having a top member and a body, wherein the implant is expandable from a first, contracted state to a second, expanded state, coupling an insertion instrument to the expandable implant by extending the instrument through an attachment port and into a structural insert made from a different material than the body, inserting the expandable implant through an incision, and expanding the implant.

The expanding step preferably includes expanding the top member away from the body via hydraulic fluid. The coupling step may include coupling an insertion instrument to the structural insert by threading a threaded end of the insertion instrument into a threaded opening in the structural insert.

BRIEF DESCRIPTION OF THE DRAWINGS

A more complete appreciation of the subject matter of the present invention and the various advantages thereof can be realized by reference to the following detailed description, in which reference is made to the accompanying drawings.

DETAILED DESCRIPTION

In exemplary embodiments, the present disclosure is directed to a device for providing spinal support for fusion wherein the device contains a structural insert to support the loads placed on the device during insertion.

Figure 1:
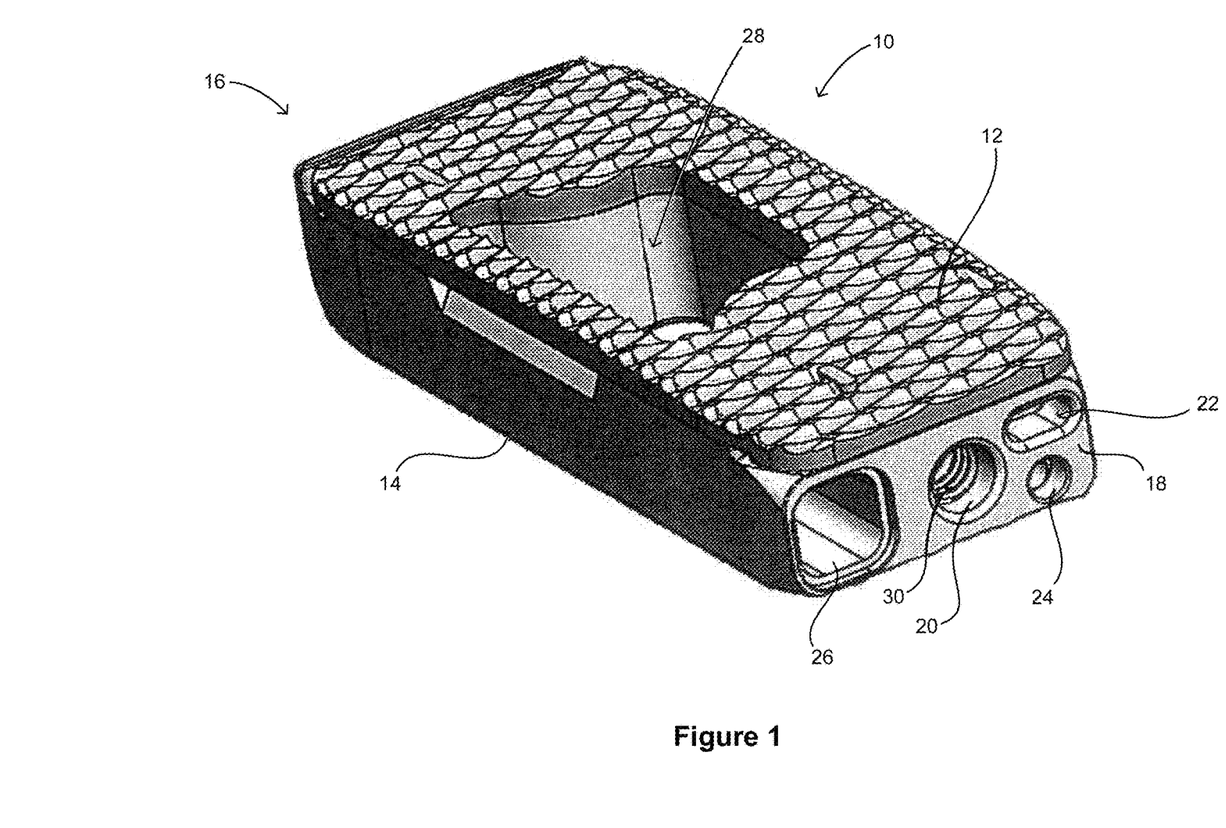
FIG. 1 is a perspective view of an embodiment of the invention.
Figure 2:
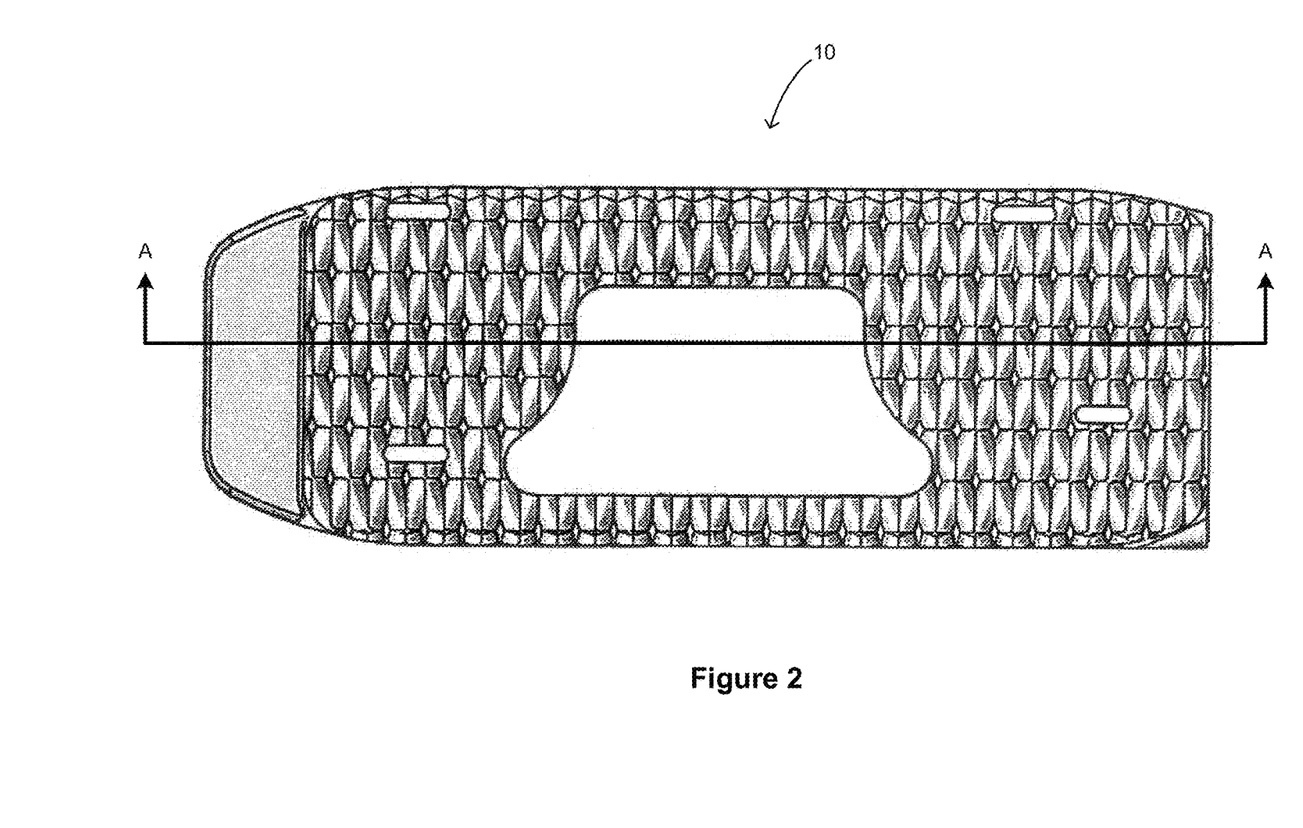
FIG. 2 is a top view of the embodiment in FIG. 1.

FIG. 1 shows an embodiment of a spinal fusion cage 10 including a top surface 12, a bottom surface 14, a distal face 16 and a proximal surface 18. The proximal surface 18 is configured to contain an attachment port 20, a torque resistant port 22, a fluid port 24 and a bone graft port 26. The attachment port is used as a means for attaching the spinal fusion cage 10 to an insertion instrument (not shown) for placing the spinal fusion cage into the prepared intervertebral space.

Figure 3:
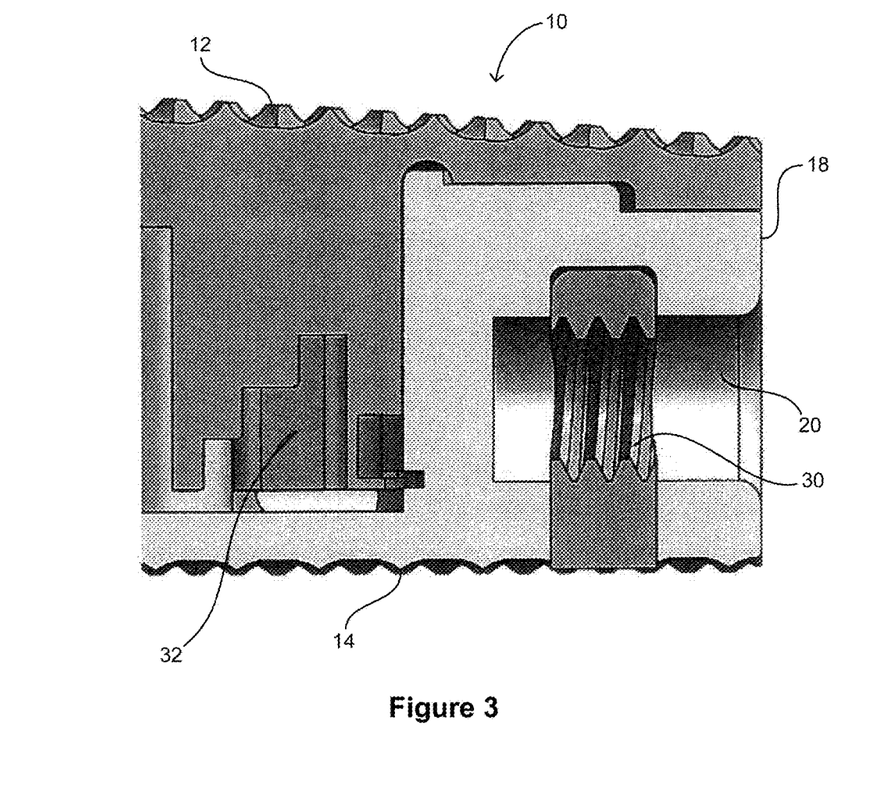
FIG. 3 is a partial cross-sectional view through Line A-A of the embodiment in FIG. 2.
Figure 4:
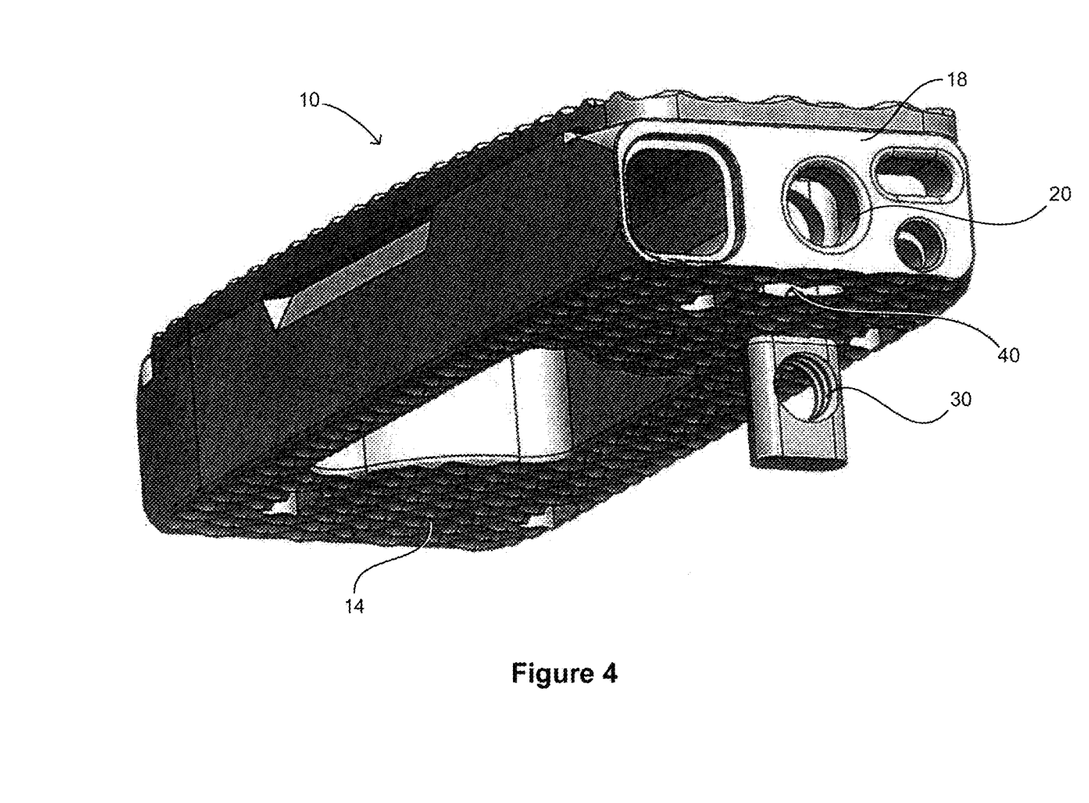
FIG. 4 is a partially exploded perspective view of the embodiment in FIG. 1.

In this exemplary embodiment, the attachment port 20 is a circular opening that is in communication with a structural threaded insert 30 (best shown in FIGS. 3 and 4). The structural threaded insert is comprised of a material that is typically stronger that the material of the body of the spinal fusion cage. For example, if the body of the implant is made of a material such as PEEK or other biocompatible polymer, the structural threaded implant 30 can be made from a metal such as a titanium alloy, a stainless steel alloy, a cobalt chromium alloy, or other suitable, biocompatible high strength materials as will be appreciated by persons of ordinary skill in the art. In this manner the structural threaded insert 30 is configured to withstand greater insertion forces placed on the spinal fusion cage 10 and thus lessen the possibility that the threaded connection for the insertion tool or the spinal fusion cage 10 itself will fail.

The fluid port 24 is configured to accept expansion fluid into the spinal fusion cage 10 when the spinal fusion cage is configured to expand hydraulically. The bone graft port 26 is configured to accept a bone graft or bone ingrowth promoting substances such as a demineralized bone matrix, the patient's own autogenous bone or cadaveric allograft bone, and direct the substance into the central bone graft opening 28.

When a structural insert 30 is provided as is shown in this exemplary embodiment, there may be a need for a torque resistant feature to help prevent rotational forces placed on the spinal fusion cage 10 from unthreading the inserter from the spinal fusion cage 10. The torque resistant port 22 as shown can be a slot or other recess configured to accept a mating torque supporting projecting tab on the inserter. Alternately, the fluid port 24 or the bone graft port 26 can be configured to accept projecting tabs from the inserter.

FIGS. 3 and 4 show how the structural threaded insert 30 is placed inside the spinal fusion cage 10. The structural threaded insert 30 may be fit into an opening 40 on the bottom surface 14 of the spinal fusion cage 10. It can be seen that the attachment port 20 of the spinal fusion cage 10 is a smooth wall that does not have threads. When attached to the inserter the structural threaded insert 30 and inserter produce a compressive load on the spinal fusion cage 10. This is desirable as the polymer material of the spinal fusion cage 10 is much stronger under the compression loads than it is under tension loads that would occur during insertion if the inserter were to be threaded directly into the polymer.

Figure 5:
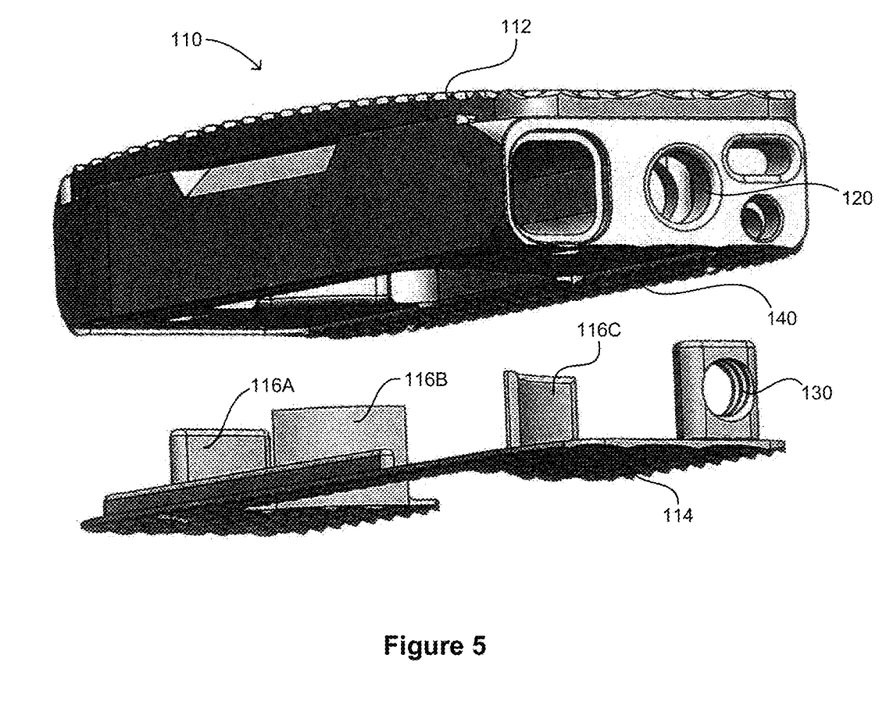
FIG. 5 is a partially exploded perspective view of an alternative embodiment of the invention.
Figure 6:
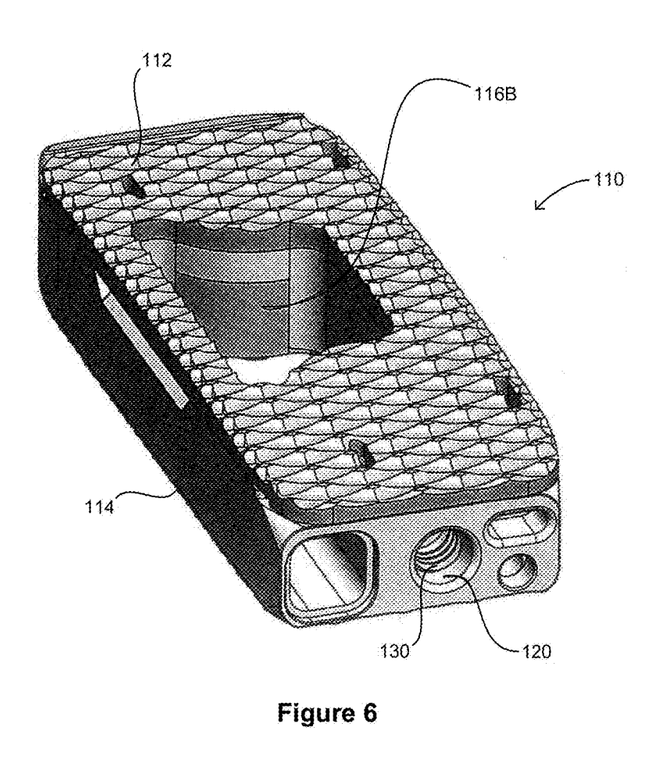
FIG. 6 is a perspective view of an embodiment in FIG. 5.

FIGS. 5 and 6 show an alternative exemplary embodiment of a spinal fusion cage 110, including a top surface 112, a bottom surface 114, and an attachment port 120. In this embodiment, the bottom surface 114 forms the base of the structural threaded insert 130, and also include one or more supporting tabs 116a-c. The spinal fusion cage 110 has an opening 140, which is configured to contain both the structural threaded insert 130 as well as the supporting tabs 116a-b and the bottom surface 114. The addition of the bottom surface 114 and the supporting tabs 116a-c distribute the insertion loads placed on the spinal fusion cage 110 over a greater area and further reduce the percentage of spinal fusion cages that would experience breaks during insertion.

Exemplary embodiments described herein are particularly well suited to be employed with selectively extendable implants such as disclosed, for example, in U.S. patent application Ser. No. 12/787,281, filed May 5, 2010, entitled "Adjustable Distraction Cage With Linked Locking Mechanisms," the disclosure of which is incorporated herein by reference in its entirety.

For instance, FIG. 3 shows a cylinder 32 configured to receive a piston (not shown). The spinal fusion cage 10 could comprise any number of cylinders (e.g. two, three, four) although only one cylinder is shown. The cylinder is pressurized by introducing a fluid through the fluid port 24 and into the cylinder 32. When the cylinder 32 is pressurized, the pistons are displaced, translating the top surface 12 away from the body 34, thereby expanding the spinal fusion cage 10. The fluid can be, for example, hydraulic fluid. It is contemplated to include mechanisms associated with the cylinder and piston arrangement to maintain their displacement, such as upper lock supports, lower lock supports, and a locking actuator. The upper and lower lock supports may have an inverted stair case and upright staircase configuration, respectively. As shown in FIG. 3, the portion of the cylinder 32 closer to the bottom surface 14 illustrates one configuration of an upper lock support. The locking actuator may be a spring for example which rotates the lower lock support relative to the upper lock support when the spinal fusion cage 10 is expanded. The lower lock support engages the upper lock support as it is rotated by the locking actuator so as to lock the spinal fusion cage in an expanded configuration.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An expandable implant comprising:
 a body having a first surface for abutting a first vertebral body, and the body having a proximal surface including a bone graft port and including an attachment port for receiving a threaded portion of an insertion instrument;
 a top member moveable with respect to the body, the top member having a second surface for abutting a second vertebral body; and
 a structural insert positioned within the body and spaced distally from the proximal surface, such that at least a portion of the body is defined between the structural insert and the proximal surface, the structural insert having a predefined threaded connection configured to detachably and rigidly couple to the threaded portion of the insertion instrument when the threaded portion is received within the attachment port, such that, when the structural insert is coupled to the insertion instrument, the orientation of the body of the implant is rigidly fixed with respect to the insertion instrument and a distal end of the insertion instrument does not exit the implant through the first surface or the second surface, wherein the structural insert is made from a different material than the body.

2. The expandable implant of claim 1, wherein the body is constructed of a polymer and the structural insert is constructed of a metal.

3. The expandable implant of claim 2, wherein the body is PEEK and the structural insert is one of titanium alloy, stainless steel alloy, and cobalt chromium alloy.

4. The expandable implant of claim 1, wherein the expandable implant is configured to expand hydraulically.

5. The expandable implant of claim 1, further comprising a bone graft opening extending through the top member and body, wherein the bone graft port is in fluid communication with the bone graft opening.

6. The expandable implant of claim 1, further comprising a torque resistant port formed in the body configured to couple to a tab on an insertion instrument to prevent the body from rotating relative to the insertion instrument.

7. The expandable implant of claim 1, wherein the attachment port has a smooth surface and is concentric with a threaded opening of the structural insert.

8. The expandable implant of claim 1, wherein the body has an opening into which the structural insert is retained.

9. An expandable implant comprising:
a body having a bone graft port;
a top member having a first surface for abutting a first vertebral body; and
a bottom member having a second surface for abutting a second vertebral body, the bottom member secured to the body, and the bottom member forming a base of a structural insert, the structural insert having a predefined threaded connection configured to detachably and securely couple to a threaded portion of an insertion instrument such that, when the structural insert is coupled to the insertion instrument, the orientation of the body of the implant is rigidly fixed with respect to the insertion instrument and a distal end of the insertion instrument does not exit the implant through the first surface or the second surface, wherein the structural insert is made from a different material than the body.

10. The expandable implant of claim 9, wherein the body is constructed of a polymer and the structural insert is constructed of a metal.

11. The expandable implant of claim 10, wherein the body is PEEK and the structural insert is one of titanium alloy, stainless steel alloy, and cobalt chromium alloy.

12. The expandable implant of claim 9, wherein the expandable implant is configured to expand hydraulically.

13. The expandable implant of claim 9, further comprising a torque resistant port formed in the body configured to couple to a tab on an insertion instrument to prevent the body from rotating relative to the insertion instrument.

14. The expandable implant of claim 9, further comprising a bone graft opening extending through the top member, body, and bottom member, wherein the bone graft port is in fluid communication with the bone graft opening.

15. The expandable implant of claim 1, wherein the structural insert is configured to couple to the threaded portion of the insertion instrument such that the threaded portion extends perpendicular to the proximal surface of the body.

16. The expandable implant of claim 1, wherein the body extends longitudinally along an axis, and wherein the structural insert is configured to couple to the threaded portion of the insertion instrument such that the threaded portion extends parallel to the axis.

17. The expandable implant of claim 9, wherein the structural insert is configured to couple to the threaded portion of the insertion instrument such that the threaded portion extends perpendicular to a proximal surface of the body.

18. The expandable implant of claim 9, wherein the body extends longitudinally along an axis, and wherein the structural insert is configured to couple to the threaded portion of the insertion instrument such that the threaded portion extends parallel to the axis.

19. The expandable implant of claim 9, wherein the bottom member includes at least one supporting tab extending into the body.

* * * * *